(12) United States Patent
Verghese et al.

(10) Patent No.: US 6,348,683 B1
(45) Date of Patent: Feb. 19, 2002

(54) QUASI-OPTICAL TRANSCEIVER HAVING AN ANTENNA WITH TIME VARYING VOLTAGE

(75) Inventors: Simon Verghese, Charlestown; K. Alexander McIntosh, Groton, both of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/072,362

(22) Filed: May 4, 1998

(51) Int. Cl.[7] .............................................. H01L 31/00
(52) U.S. Cl. .................................................. 250/214.1
(58) Field of Search ........................ 260/214.1, 227.19, 260/227.23, 227.24, 227.27; 343/742, 743; 359/152, 154, 151; 356/346–349

(56) References Cited

U.S. PATENT DOCUMENTS

| | | | |
|---|---|---|---|
| 3,506,363 A | 4/1970 | Rosfelder | 356/147 |
| 3,562,533 A | 2/1971 | Doyle et al. | 250/199 |
| 3,571,549 A | 3/1971 | Doyle et al. | 200/199 |
| 3,578,864 A | 5/1971 | Ross | 356/32 |
| 3,899,428 A | 8/1975 | Auston et al. | 250/199 |
| 4,033,882 A | 7/1977 | Fletcher et al. | 250/199 |
| 5,056,111 A | 10/1991 | Duling, III et al. | 375/37 |
| 5,119,035 A | 6/1992 | Goy et al. | 324/639 |
| 5,493,433 A | 2/1996 | Prucnal et al. | 359/123 |
| 5,493,719 A | 2/1996 | Smith et al. | 455/325 |
| 6,144,679 A | * 11/2000 | Herman et al. | 372/21 |

OTHER PUBLICATIONS

S. Verghese et al., "Highly Tunable Fiber–Coupled Photomixers with Coherent Terahertz Output Power" *IEEE Trans. on Microwave Theory & Tech.* 45(8):1301–1309 (1997) (Month Unknown).

S. Anderson, "Researchers Map Real–Time 2–D Terahertz Images" *Laser Focus World*, pp. 30–31, Jul. 1996.
R. DeMeis, "Terahertz Pulses Create Diffraction–Limited Images" *Laser Focus World*, p 15, Jul. 1995.
R. H. Jacobsen et al., "Real–Time Chemical Recognition of Gas Mixtures Using Optoelectronic Terahertz Waveforms" Proceedings of Ultrafast Electronics and Optoelectronics TOPS 13 (1997) (Month Unknown).
D. M. Mittleman et al., "T–Ray Imaging" *IEEE J. of Selected Topics in Quantum Electronics*, Special Issue on Ultrafast Electronics, Photonics and Optoelectronics (1997) (Month Unknown).
Nuss, "Chemistry is Right for T–Ray Imaging," *IEEE Circuits and Devices Magazine*, vol. 12, No. 2, p. 25–30, Mar. 1996.

(List continued on next page.)

*Primary Examiner*—Que T. Le
(74) *Attorney, Agent, or Firm*—Testa, Hurwitz & Thibeault, LLP (57) ABSTRACT

A transceiver for transmitting and receiving high frequency radiation is described. The transceiver includes a first light source that generates radiation at a first frequency and a second light source that generates radiation at a second frequency. The first and the second light source have a difference frequency that is approximately equal to the difference between the first and the second frequencies. The transceiver also includes a transmitter that comprises a first photomixer that is optically coupled to the first and the second light source. A first antenna that radiates a signal at the difference frequency is electrically coupled to the first photomixer. The transceiver also includes a receiver that comprises a second antenna positioned to receive the signal radiated by the first antenna. The second antenna generates a time varying voltage in response to the signal. A second photomixer is electrically coupled to the second antenna and optically coupled to the first and the second light source. The second photomixer generates a current signal in response to the time varying voltage generated by the second antenna.

33 Claims, 6 Drawing Sheets

OTHER PUBLICATIONS

Brown et al., "Coherent Terahertz Generation using Low-–Temperature–Grown GaAs Photomixers," *CLEO '95*, (JWD3 (Invited)), vol. 15, 1995 Technical Digest Series, Conference Edition, p. 230, 1995. (Month Unkown).

McIntosh et al., "Terahertz Photomixing with Diode Lasers in Low–Temperature–Grown GaAs," *Appl. Phys. Lett.*, vol. 67, No. 26, p. 3844–3846, Dec. 25, 1995.

Pine et al., "A Terahertz Photomixing Spectrometer: Application to $SO_2$ Self Broadening" *J. of Molecular Spectroscopy*, vol. 175, No. 1, p. 37–47 (1996). (Month Unknown).

Verghese et al., "Generation and detection of cw terahertz waves using two photomixers," p. 1–12, submitted to APL on Jul. 23, 1998.

* cited by examiner

QUASI-OPTICAL TRANSCEIVER HAVING AN ANTENNA WITH TIME VARYING VOLTAGE

GOVERNMENT SUPPORT

This invention was made with government support under Contract Number F19628-95-C-0002 awarded by the Department of the Air Force. The government has certain rights in the invention.

FIELD OF THE INVENTION

The invention relates generally to the field of high frequency transceivers. In particular, the invention relates to RF and quasi-optical transceivers and to methods of transmitting and receiving RF and quasi-optical radiation for applications that include spectroscopy, imaging, network analysis, radar and communications.

BACKGROUND OF THE INVENTION

Photoconductive "Auston" switches that convert femtosecond optical pulses into high frequency electrical pulses have been used to generate quasi-optical signals. These switches are constructed from undoped semiconducting materials such as GaAs, InP, and silicon, which are normally insulating. In operation, the semiconductors are irradiated by femtosecond laser pulses which cause electrons and holes to be injected into the conduction and valence bands of the semiconductors thereby making the semiconductors highly conductive. The "Auston" switch has been used in systems to perform high-resolution spectroscopy. These systems, however, are large and expensive and have relatively low power per unit spectral bandwidth.

Another method of generating quasi-optical signals is to use an optical-heterodyne converter or photomixer source. Photomixer sources are compact solid-state sources that use two single frequency tunable lasers, such as diode lasers, to generate a terahertz difference frequency by photoconductive mixing in a photoconductive material. Photomixer sources using low-temperature-grown (LTG) GaAs have been used to generate coherent radiation at frequencies up to 5 THz.

Photomixer sources have been used in conjunction with cryogenic detectors, such as bolometers, to construct local oscillators and high-resolution gas spectrometers. These devices, however, suffer from having to use cryogenic materials. Other sources such as backward-wave-oscillators used in conjunction with Schottky mixers or thermal detectors are physically large and expensive. Other sources such as molecular gas lasers are discrete frequency sources that are also large and expensive.

SUMMARY OF THE INVENTION

It is a principal object of this invention to provide a quasi-optical transceiver that can be constructed with commercially available components and that is compact, inexpensive, and does not require the use of cryogenics. It is another principal object of this invention to provide a quasi-optical transceiver that has high spectral brightness. It is another principal object of this invention to provide a quasi-optical transceiver that is frequency agile, continuous tuning, and relatively insensitive to source frequency drift. It is another principal object of this invention to provide a quasi-optical high resolution spectrometer with a high signal-to-noise ratio that can be constructed from a photomixer transceiver. Other principal objects of this invention are to provide an imaging system, network analyzer, radar, and a communication system that can be constructed from a photomixer transceiver.

A principal discovery of this invention is that a high frequency transceiver can be constructed from two photomixers pumped by the same optical sources and that such a transceiver has numerous advantages over the prior art. These advantages include high spectral brightness, frequency agility, continuously tuning, and relative insensitivity to source frequency drift. Another principal discovery of the present invention is that such a transceiver may be used to perform high-resolution spectroscopy with a state-of-the-art signal-to-noise ratio, but with reduced physical size and cost.

Accordingly, the present invention features a transceiver for transmitting and receiving high frequency radiation. The transceiver includes a first light source that generates radiation at a first frequency and a second light source that generates radiation at a second frequency. The first and the second light source have a difference frequency that is approximately equal to the difference between the first and the second frequencies. A transmitter includes a first photomixer that is optically coupled to the first and the second light source. A first antenna is electrically coupled to the first photomixer. In operation, the first antenna radiates a signal generated by the first photomixer at the difference frequency.

A receiver includes a second antenna positioned to receive the signal radiated by the first antenna. The second antenna generates a time varying voltage in response to the signal. A second photomixer is electrically coupled to the second antenna and is optically coupled to the first and the second light source. The second photomixer generates a current signal in response to the time varying voltage generated by the second antenna.

The transceiver of the present invention has numerous applications including spectroscopy, imaging, network analysis, radar and communications. The present invention also features a real time spectrometer, an imaging system, a network analyzer, a radar and a communications system. In addition, the present invention features methods of performing real time spectroscopy, imaging an object, performing network analysis, forming a Doppler radar image and communicating.

BRIEF DESCRIPTION OF THE DRAWINGS

This invention is described with particularity in the appended claims. The above and further advantages of this invention may be better understood by referring to the following description taken in conjunction with the accompanying drawings, in which:

FIG. 1a is a schematic diagram of a photomixer transceiver that embodies the invention. FIG. 1b illustrates an enlarged schematic diagram of the photomixers and antennas of FIG. 1a.

DETAILED DESCRIPTION

Figures 1A, 1B:
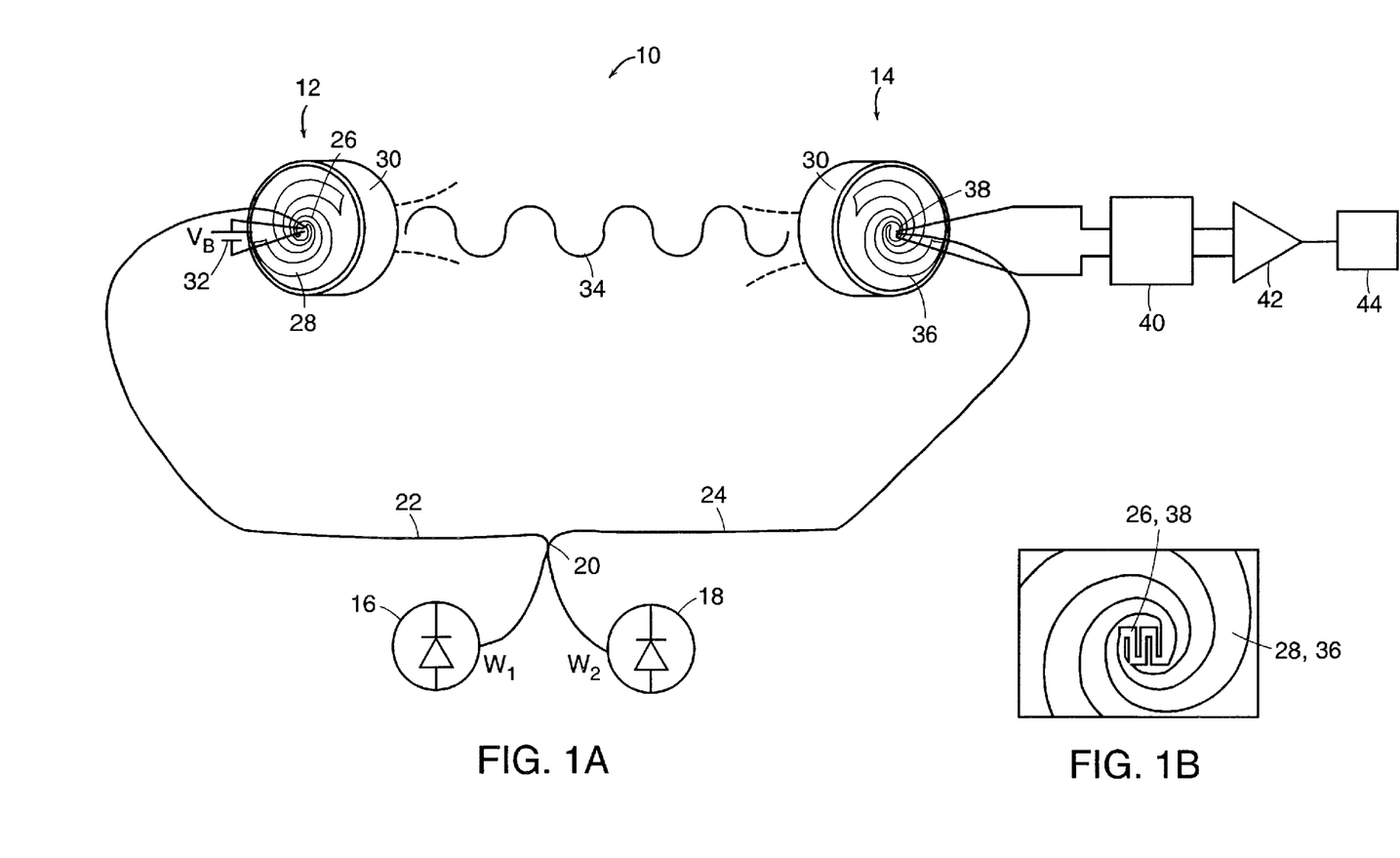

FIG. 1a is a schematic diagram of a photomixer transceiver 10 comprising a photomixer transmitter 12 and a photomixer receiver 14 that embodies the invention. The transceiver 10 includes a first 16 and a second source 18 of coherent radiation that generates a first and a second beam of coherent light at a first and a second distinct frequency $\omega_1$ and $\omega_2$, respectively. The first and second beam may be continuous wave (CW) or pulsed. In one embodiment, the first source 16 and the second source 18 include diode lasers that emit near-infrared radiation. Each diode laser may be a distributed-Bragg-reflector (DBR) or distributed feedback (DFB) diode laser. Such lasers are commercially available and relatively inexpensive.

The photomixer transceiver 10 includes a beam splitter 20 that separates each of the first and the second beams of light into a first 22 and a second optical path 24 that terminate at the photomixer transmitter 12 and the photomixer receiver 14, respectively. The first and the second beam of light may be guided through the first 22 and the second optical path 24 by an optical fiber or may be focused along the first 22 and the second optical path 24 by lenses (not shown).

The photomixer transmitter 12 includes a first photomixer 26 that, in one embodiment, includes a low-temperature-grown (LTG) GaAs photoconductive material. LTG GaAs is a particularly good photoconductive material for high speed photoconductive correlators because it exhibits very short electron-hole lifetimes (<1 ps), has high electrical breakdown field (>$10^6$ V/cm), and has high mobility relative to other photoconductors having comparable lifetimes. In one embodiment, the first photomixer 26 includes a photoconductor having an active region that has dimensions of approximately 20×20-$\mu$m.

The first photomixer 26 is optically coupled to the first optical path 22. The first photomixer 26 may be coupled to the first optical path 22 by numerous methods known in the art. In one embodiment, an optical fiber defines the first optical path and the first photomixer 26 is coupled to the optical fiber by butt coupling. In another embodiment, the first optical path is defined by at least one lens (not shown) and the first photomixer 26 is positioned in the first optical path 22. In operation, the first and second optical beams in the first optical path 22 beat against each other and modulate the conductance of the first photomixer 26 at a difference frequency $\Omega=\omega_2-\omega_1$.

The first photomixer 26 is biased with a voltage source 32 that generates a DC or an AC voltage. The bias voltage causes a current to flow through the first photomixer 26 at frequency $\Omega$. The first photomixer 26 may be biased by numerous methods known in the art. In one embodiment, the first photomixer 26 is embedded in a transmission line or waveguide geometry such as a co-planar waveguide and a bias voltage is applied with a bias T. The co-planar waveguide may transition into a 50-$\omega$ coaxial line (not shown) that connects the photomixer transmitter 12 to the photomixer receiver 14. In another embodiment, the first photomixer 12 is connected directly to the voltage source 32. In operation, the voltage source 32 biases the first photomixer 26 to generate a current having a frequency approximately equal to the difference frequency $\Omega$.

A first antenna 28 is electrically coupled to the first photomixer 26. The first antenna 28 is shown as a spiral antenna 28. Alternately, the first antenna 28 may be an interdigitated electrode antenna. In one embodiment, the interdigitated electrode antenna is approximately 0.2-$\mu$m wide by approximately 0.4 to 0.6 $\mu$m. A dielectric lens 30, such as a silicon lens, may be used to focus the transmitted radiation. Numerous other antenna structures, such as planar antennas and horn antennas, that are known in the art, may also be used.

In operation, the first antenna 28 radiates a signal corresponding to the current generated by the first photomixer 26. The photomixer transmitter 12 can be represented as a transmitter equivalent circuit comprising the series combination of the first photomixer conductance G(t) at the difference frequency $\Omega$, the voltage source 32, and the first antenna impedance.

The signal propagates through a medium 34 placed between the photomixer transmitter 12 and the photomixer receiver 14. The photomixer receiver 14 includes a second antenna 36 that is positioned to receive the signal radiated by the first antenna 28. A dielectric lens 30 may direct the signal radiated by the first antenna 28 to the second antenna 36, which is shown as a spiral antenna. The second antenna 36 generates a time varying voltage in response to the signal. As described in connection with the first antenna 28, the second antenna 36 may also be an interdigitated electrode antenna, a planar antenna, or a horn antenna.

A second photomixer 38 is electrically coupled to the second antenna 36 and is optically coupled to the second optical path 24 by numerous methods known in the art as described in connection with the first photomixer 26. In one embodiment, the second photomixer 38 comprises LTG GaAs. In operation, a conductance (not shown) of the second photomixer 38 is modulated at the difference frequency $\Omega$ in response to the first 16 and the second light source 18. The optical beating of the first and the second light beams by way of path 24 periodically raises the photoconductance of the second photomixer 38 such that a current signal is generated in response to the time varying voltage generated by the second antenna 36.

In one embodiment, an intermediate frequency (IF) amplifier 40 is electrically coupled to the second photomixer 38 and amplifies intermediate frequencies generated by the second photomixer 38. As described herein, an output of the IF amplifier can be used to measure Doppler shifted signals from a target that reflects a signal transmitted by the photomixer transmitter 12.

In one embodiment, a transimpedance amplifier 42 is electrically coupled to the second photomixer 38. In operation, the transimpedance amplifier 42 generates a DC voltage in response to the current signal generated by the second photomixer 38. The DC voltage measured by the transimpedance amplifier 42 is directly proportional to the radiation incident on the photomixer receiver 14 as described below.

The photomixer receiver 14 coupled to the transimpedance amplifier 42 can be represented as a receiver equivalent circuit comprising the series combination of the second photomixer conductance G(t) at the difference frequency $\Omega$, the second antenna impedance, and the transimpedance amplifier 42. The radiation received by the second antenna 36 induces a time-varying voltage V(t) across the second antenna impedance. The current flowing through the receiver equivalent circuit is approximately V(t)G(t). The current will have a time-varying term at frequency $2\Omega$ and a DC term that is proportional to V(t). The DC term detected by the transimpedance amplifier 42 is directly proportional to the radiation incident on the second antenna 36.

Experiments were performed to verify that homodyne detection does occur in the photomixer receiver 14. Received signals scaled linearly with the DC bias voltage. The magnitude of the current generated by the second photomixer 38 was in good agreement with predictions from a theoretical model that accounted for the impedance mismatch between the photomixers and the transmission line.

A processor 44 may be in communication with the second photomixer 38 either directly or through the IF amplifier 40 and/or the transimpedance amplifier 42. The processor 44 processes the current signal generated by the second photomixer 38, the IF frequency signal generated by the IF amplifier 40, and/or the DC voltage signal generated by the transimpedance amplifier 42. There are numerous application of RF and quasi-optical transceivers that require processing of the received signals. These applications include spectroscopy, imaging, network analysis, radar and communications.

FIG. 1b illustrates an enlarged schematic diagram of the photomixers and antennas of FIG. 1a. As described above, although the first 28 and second antenna 36 are shown as spiral antennas, they may also be interdigitated electrode antennas, planar antennas, or horn antennas.

The photomixer transceiver 10 of FIG. 1 has numerous advantages over the prior art. One advantage is that the photomixer transceiver 10 is highly frequency agile and can be continuously tuned. Some applications such as spectroscopy require the transceiver to operate at more than one difference frequency. If the first 16 and the second source 18 comprise diode lasers, the emission wavelength of one of the diode lasers can be temperature tuned.

Another advantage of the photomixer transceiver 10 is that it is relatively insensitive to frequency drift occurring in the first 16 and the second source 18. Any drift in the frequency stability of the first 16 and the second source 18 will change the difference frequency Ω and modulate the conductance of both the first 26 and the second photomixer 38 at the same changed difference frequency Ω. Therefore, any frequency drift in the transmitted signal is exactly tracked by the frequency drifts in the photomixer receiver 14.

The present invention also features a method of transmitting and receiving RF and quasi-optical radiation. A first and a second light source that generates a first and a second beam of light at a first frequency and a second frequency, respectively is provided. The first and second light sources may be pulsed or a CW light source. In response to the first and the second light beam, a conductance of a first photomixer is modulated at a difference frequency that is approximately equal to the difference between the first and the second frequencies. The modulated conductance generates a signal having the difference frequency. The signal is transmitted through a medium.

The signal transmitted through the medium is received and a time varying voltage is generated in response to the signal. In response to the first and the second light beam, a conductance of a second photomixer is modulated at the difference frequency. A current signal is generated in response to the time varying signal received by the second antenna and the modulated conductance of the second photomixer. A DC voltage may be detected in response to the current signal generated.

The present invention also features a method of forming a Doppler radar image. The first antenna radiates a signal at the difference frequency. The signal is reflected off of a moving target object (not shown) where it is Doppler-shifted. The resulting Doppler-shifted signal emanates from the target object in the direction of the second antenna. The Doppler-shifted signal is received by the second antenna 36. The second photomixer 38 generates a current signal in response to the time varying voltage generated by the second antenna 36. The IF amplifier 40 amplifies the IF signals in the current signal. The processor 44 processes the IF signals as radar data. The maximum Doppler-shift that can be measured is determined by the bandwidth of the IF amplifier 40 and by the intrinsic linewidth of the first and the second light source (typically <100 kHz for diode lasers).

Figure 2:
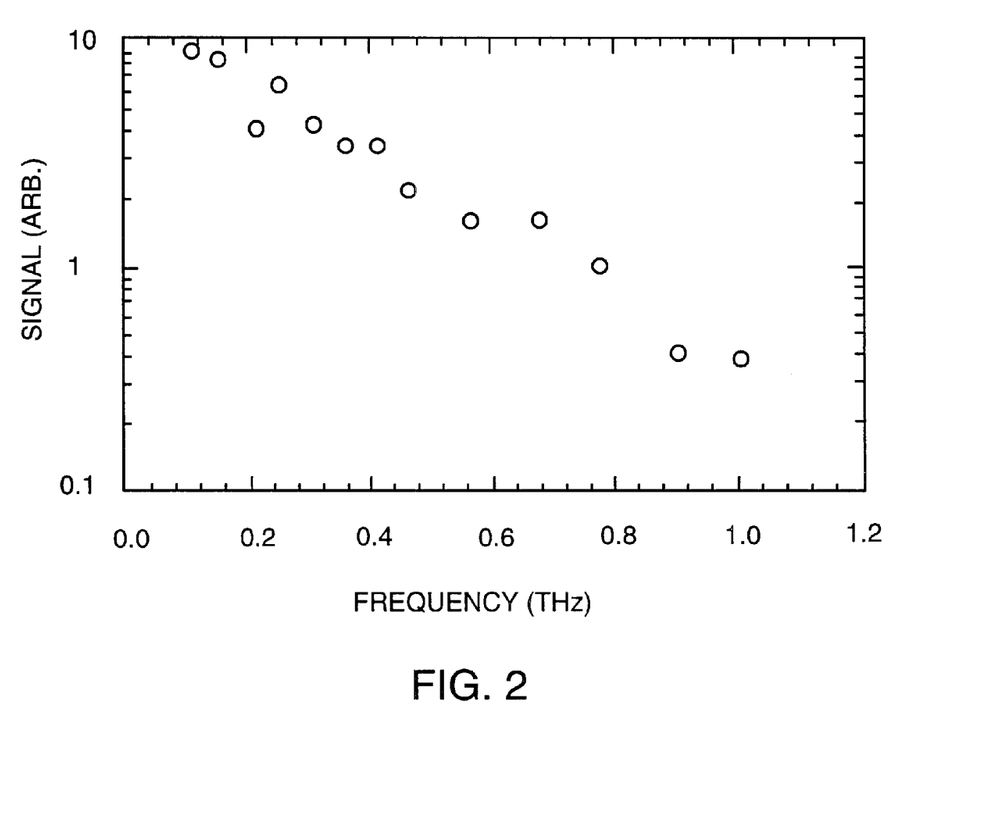
FIG. 2 illustrates experimental data for the photomixer transceiver of FIG. 1.

FIG. 2 illustrates experimental data for the photomixer transceiver of FIG. 1. The first light source was a diode laser emitting radiation at approximately 850 nm. The second light source was a tunable diode laser with a center frequency of approximately 852 nm. A silicon hyper-hemispherical lens was used to focus the transmitted radiation onto a spiral antenna. The area of the receiver photomixer 38 was approximately 64 square microns. The signal detected with the spiral antenna is plotted as a function of difference frequency. Radiation was detected from approximately 0.1 to 1.0 Terahertz.

Figure 3:
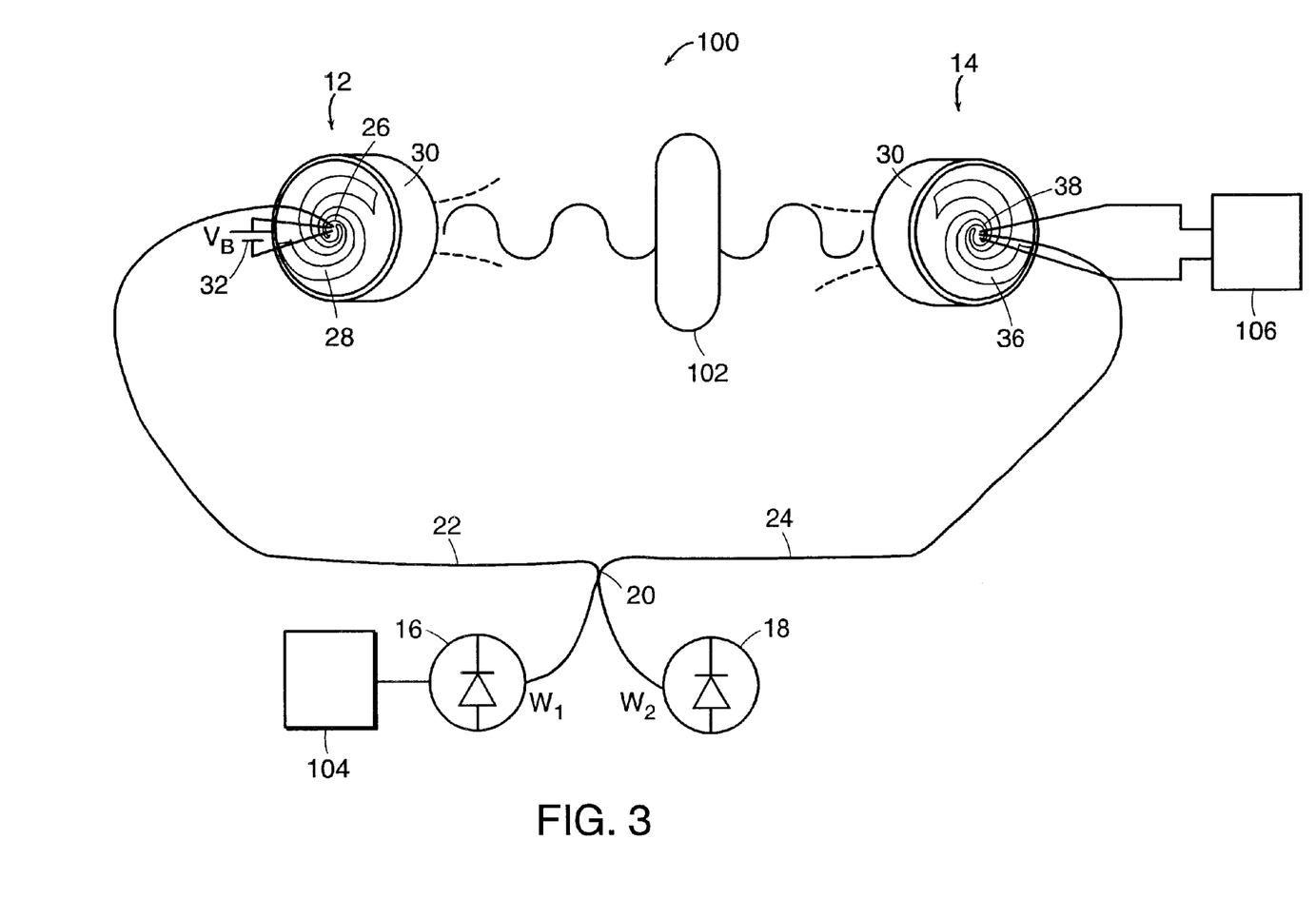
FIG. 3 illustrates a schematic diagram of a spectrometer that uses the photomixer transceiver that embodies the invention.

FIG. 3 illustrates a schematic diagram of a spectrometer 100 that uses the photomixer transceiver that embodies the invention. The transceiver of FIG. 1 is adapted for use as a spectrometer. A medium 102 to be analyzed is positioned in the path of the signals generated by the photomixer transmitter 12. The medium to be analyzed may be any medium with at least some transmission in the RF and quasi-optical region. The medium may be a solid, liquid, gas or even a plasma. Gases, however, have sharp and characteristic absorption lines in the quasi-optical region and, therefore are easy to analyze with a quasi-optical spectrometer.

The signals generated by the photomixer transmitter 12 at the difference frequency propagate through the medium 102 and are received by the photomixer receiver 14. The difference frequency can be changed by adjusting the frequency of at least one of the first 16 or second sources 18 with a frequency tuning device 104 such as a temperature controller. An analyzer 106 samples and measures at least one of amplitude or phase of the current signal generated by the photomixer receiver 14. The analyzer 106 then determines at least one of the absorption or dispersion characteristics of the medium from the amplitude or phase measurement. The analyzer 106 may also identify the medium or certain properties of the medium.

Many materials have characteristic absorption frequencies that can be used for identification. Also, many materials have frequency dependent refractive indices that will produce frequency chirped signal in the quasi-optical region that can be used for identification. Some gases also have multiple absorption lines that result in beating of two or more frequencies that generate oscillatory waveforms that are unique. From the unique oscillatory waveforms it can unambiguously be determined which gases are present.

The present invention also features a method of performing real time spectroscopy by CW or pulse laser photoconductive sampling. The method includes providing a first and a second light source that generates a first and a second beam of light at a first and a second frequency, respectively. In response to the first and the second light beam, a conductance of a first photomixer is modulated at a difference frequency that is approximately equal to the difference between the first and the second frequencies. The modulated conductance generates a signal having the difference frequency. The signal is transmitted through a medium to be analyzed.

The signal transmitted through the medium is received and a time varying voltage is generated in response to the signal. In response to the first and the second light beam, a conductance of a second photomixer is modulated at the difference frequency. A current signal is generated in response to the time varying signal received by the second antenna and the modulated conductance of the second photomixer.

At least one of amplitude or phase of the current signal is measured. At least one of the absorption or dispersion characteristics of the medium is determined from the amplitude or phase measurement. The absorption or dispersion characteristics of the medium may be determined by measuring a frequency chirp in the current signal. From the absorption or dispersion characteristics, the presence of a particular medium can be determined. The method may be repeated for different difference frequencies by first changing at least one of the first or the second frequency and then repeating the steps of the method.

The method of performing real time spectroscopy according to this invention has numerous advantages over the prior art. One advantage is that the method has high spectral brightness and, therefore, high sensitivity because it uses high brightness diode lasers. For spectroscopy applications that require narrow-resolution linewidth (<1 MHz), this method has significantly higher spectral brightness (~$10^6$ times higher) than prior art time-domain sampling methods. Another advantage is that a spectrometer using this method would be relatively compact and inexpensive because it uses commercially available diode lasers. In addition, such a spectrometer would operate at room temperature and would not require the use of a cryogenically cooled detector.

The spectrometer of the present invention is useful for many applications including real-time trace gas monitoring. Such monitoring is important for the semiconductor fabrication and other manufacturing industries and for numerous military applications. Such monitoring is also important for pollution monitoring. The high spectral brightness and simplicity of the spectrometer of the present invention are important advantages over prior art Fourier transform spectrometers or photoconductive-switch systems that use pulsed lasers.

Figure 4:
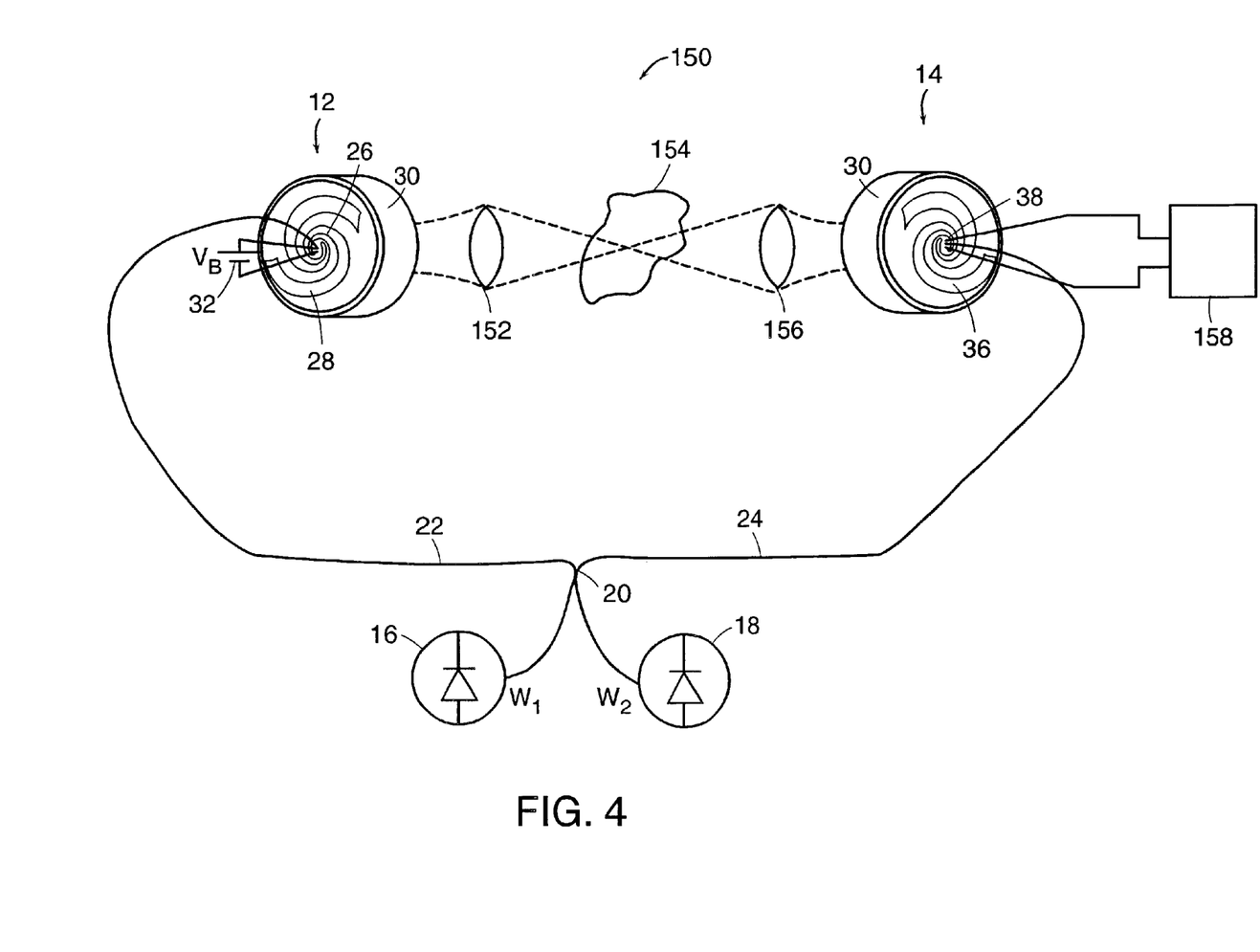
FIG. 4 illustrates a schematic diagram of an imaging system that uses the photomixer transceiver that embodies the invention.

FIG. 4 illustrates a schematic diagram of an imaging system using the photomixer transceiver that embodies the invention. The photomixer transceiver of FIG. 1 is adapted for use as an imaging system. The signal generated by the photomixer transmitter 12 is focused by a first dielectric lens 152 to an object 154 to be imaged. The signal can be focused to the diffraction limit.

The object 154 to be imaged is typically partially absorbing to quasi-optical radiation. Many materials have frequency dependent absorption and dispersion in the quasi-optical region. Polar liquids, such as water or solvents, are typically highly absorbing in this region. In contrast, most dry, nonmetallic objects such as plastics, paper, cardboard, glass, and many other dielectric materials are highly transparent in the quasi-optical frequency range.

The signal propagates through the object 154 to a second dielectric lens 156. The second lens 156 focuses the signal onto the second antenna 36. The current signal generated by the second photomixer contains both amplitude and phase information about the object 154 that can be used to create an image of the object 154. An image processor 158 processes the amplitude and phase information and generates imaging data.

The imaging system of the present invention is useful for inspection. There are many applications in packaging, quality control, and security, where it is important to look through some materials to reveal certain objects. For example, an imaging system of the present invention can be used to scan envelopes for letter bombs or to scan passengers for weapons, explosives or drugs.

The imaging system of the present invention is useful for detecting small amounts of water or solvents. There are many applications that require accurate measurement of moisture content, either in a manufacturing process or to ensure quality. One example is in the food processing industry because moisture in many foods has to be maintained within certain limits. Another example is in the paper industry.

The imaging system of the present invention is also useful for determining the doping profile in semiconductor and superconductor materials. The carriers that conduct currents in semiconductors and superconductors are highly absorbing to quasi-optical frequencies. An imaging system according to the present invention has a high sensitivity to charge carriers in semiconductor materials.

The imaging system of the present invention is also useful for measuring the frequency dependent absorption and the frequency dependent refractive index of a material. In the quasi-optical frequency range, the absorption coefficient and the dielectric constant of many materials usually varies significantly. Signals transmitted through the material will be attenuated according to the material's frequency dependent absorption. The signals may also be frequency chirped according to the material's frequency dependent refractive index. For example, if the refractive index rises with frequency, low frequencies will travel faster through the material than high frequencies. Therefore, the low frequencies end up at the leading edge of the pulse, while the high frequencies trail behind the leading edge of the pulse.

The present invention also features a method of imaging an object. The method includes providing a first and a second light source that generates a first and a second beam of light at a first and a second frequency, respectively. A conductance of a first photomixer is modulated at a difference frequency that is approximately equal to the difference between the first and the second frequencies in response to the first and the second light beam to generate a signal having the difference frequency. The signal is transmitted through an object to be imaged and then received. The signal may be transmitted through a predetermined position on the object.

A time varying voltage is generated in response to the signal. A conductance of a second photomixer is modulated at the difference frequency in response to the first and the second light beam. A current signal is generated in response to the signal received and the modulated conductance of the second photomixer. The current signal may be converted to digital data or it may be frequency converted to a lower frequency. At least one of the amplitude or the phase of the current signal is measured and processed to form an image of the object.

One advantage of the imaging system of the present invention is that it provides high spectral brightness. Numerous applications, such as imaging the strength of a narrow band signal from a molecular absorption process, require high spectral brightness.

Figure 5:
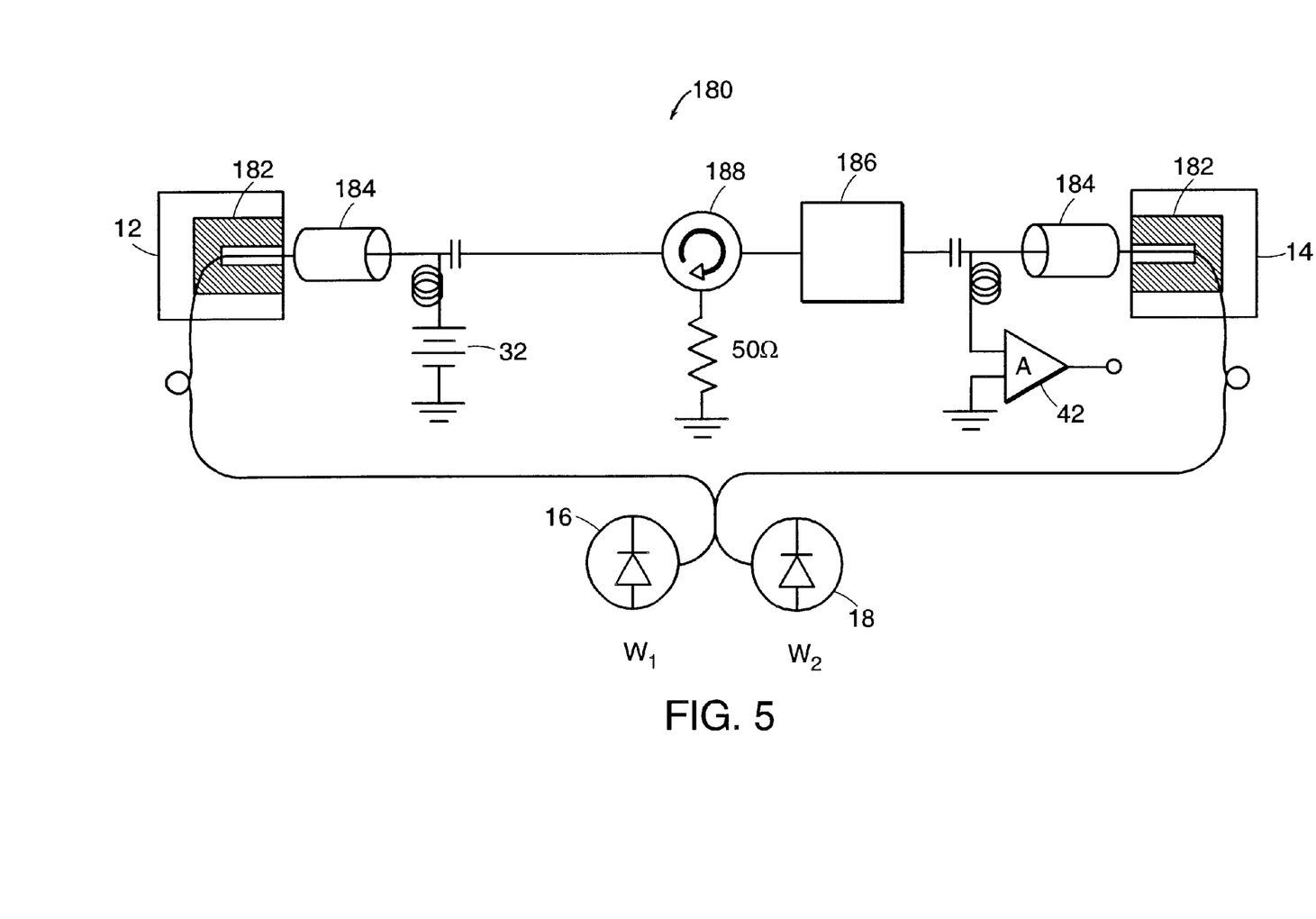
FIG. 5 illustrates a schematic diagram of a network analyzer that uses the photomixer transceiver that embodies the invention.

FIG. 5 illustrates a schematic diagram of a network analyzer 180 that uses the photomixer transceiver that embodies the invention. The transceiver of FIG. 1 is adapted for use as a network analyzer. The photomixer transmitter 12 and the photomixer receiver 14 are both mounted in co-planar waveguides 182. The co-planar waveguides 182 may transition into a 50-Ω coaxial transmission line 184 that connects the photomixer transmitter 12 and the photomixer receiver 14 to a device 186 under test. Numerous other waveguide structures known in the art can be used to mount the photomixer transmitter 12 and the photomixer receiver 14 and to connect them to the device 186 under test. An isolator 188 may be used to eliminate reflections and standing waves in the coaxial transmission line 184.

In one embodiment, a second photomixer receiver (not shown) is coupled to a reflection port of the device 186 under test and receives signals reflected from the device 186 under test. Using the first 14 and the second photomixer receivers allows both transmission and reflection measurements of the device 186 under test without reconfiguring the device. In another embodiment, an additional photomixer transmitter (not shown) and an additional photomixer receiver (not shown) are included to fully characterize a two port device under test without reconfiguring the device.

The transfer characteristic of a narrow bandpass filter has been measured with the network analyzer of FIG. 5 and the results agreed with the transfer characteristic measured using a commercial microwave spectrum analyzer.

The present invention also features a method of network analysis. The method includes providing a first and a second light source that generates a first and a second beam of light at a first and a second frequency, respectively. A conductance of a first photomixer is modulated at a difference frequency that is approximately equal to the difference between the first and the second frequencies in response to the first and the second light beam to generate a signal having the difference frequency. The signal is transmitted through or reflected from a network to be analyzed and then received.

A time varying voltage is generated in response to the signal. A conductance of a second photomixer is modulated at the difference frequency in response to the first and the second light beam. A current signal is generated in response to the signal received and the modulated conductance of the second photomixer. At least one of the amplitude or the phase of the current signal is measured and processed to determine at least one of a transmission or a reflection parameter of the network such as the scattering parameter.

Figure 6:
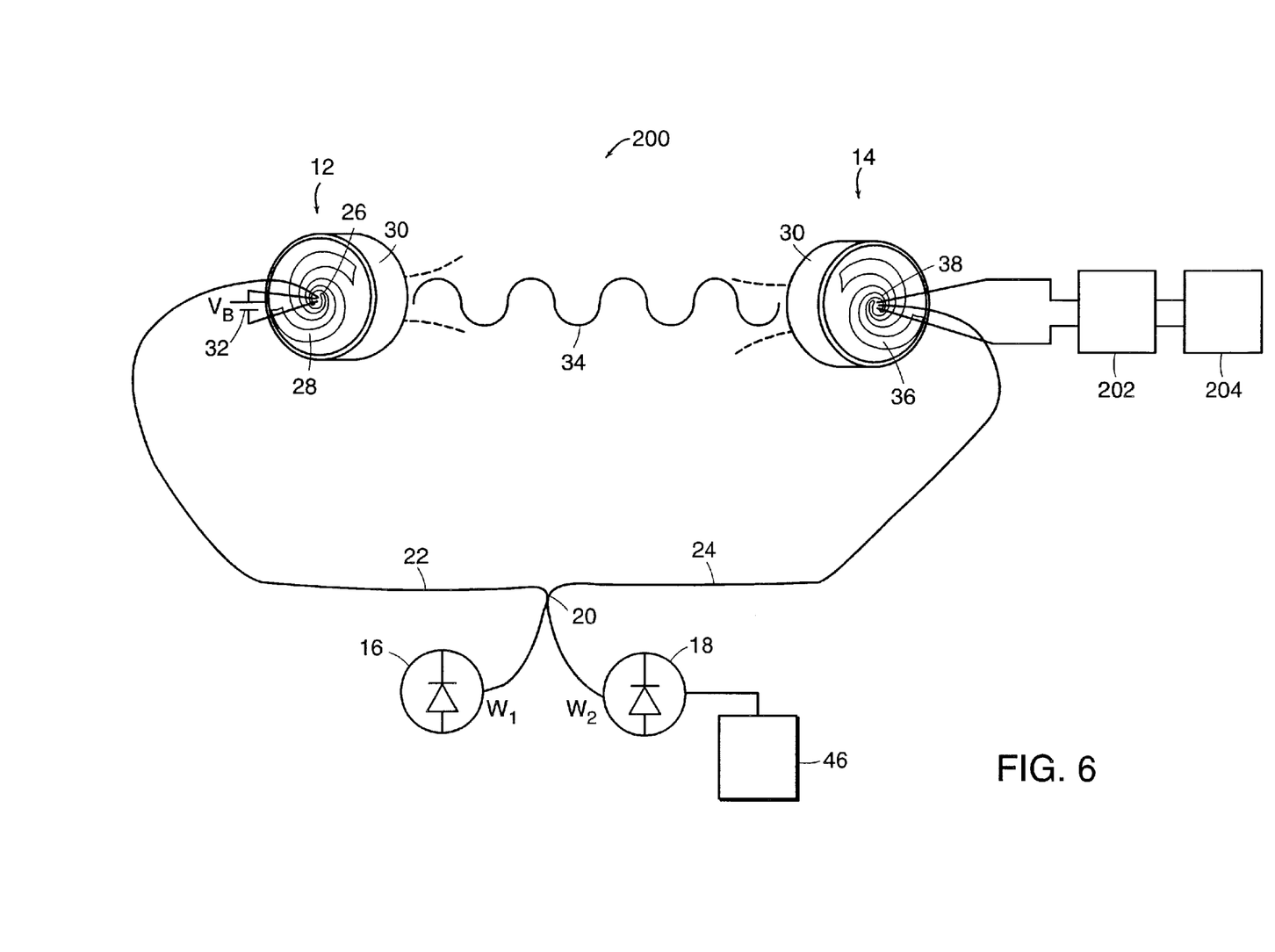
FIG. 6 illustrates a schematic diagram of a communications system that uses the photomixer transceiver that embodies the invention.

The present invention also features apparatus and methods of quasi-optical communications. FIG. 6 illustrates a schematic diagram of a communications system 200 that uses the photomixer transceiver that embodies the invention. The transceiver of FIG. 1 is adapted to communicate data.

A modulator 201 is coupled to at least one of the first 16 or the second source 18. The modulator 201 is used to modulate onto the first and/or the second beam a data stream to be communicated. A down converter 202 may be used to downconvert the modulated signal received by the photomixer receiver 14. A demodulator 204 is used to demodulate the data from the received signal.

A method of quasi-optical communications according to the present invention includes providing a first and a second light source that generates a first and a second beam of light at a first and a second frequency, respectively. The first and the second beam of light are modulated with data. A conductance of a first photomixer is modulated at a difference frequency that is approximately equal to the difference between the first and the second frequencies in response to the first and the second beam of light to generate a modulated signal having the difference frequency. The modulated signal is transmitted through a medium which may be a transmission line or which may be free space.

The modulated signal is received and a time varying voltage is generated in response to the modulated signal. A conductance of a second photomixer is modulated at the difference frequency in response to the first and the second light beam. A current signal is generated in response to the modulated signal received and the modulated conductance of the second photomixer. The current signal is then downconverted and demodulated.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A transceiver comprising:
   a) a first light source generating radiation at a first frequency;
   b) a second light source generating radiation at a second frequency, the first and the second light source having a difference frequency approximately equal to the difference between the first and the second frequencies;
   c) a transmitter comprising:
      i) a first photomixer optically coupled to the first light source and the second light source; and
      ii) a first antenna electrically coupled to the first photomixer, the first antenna radiating a signal having a frequency substantially equal to the difference frequency; and
   d) a receiver comprising:
      i) a second antenna positioned to receive the signal radiated by the first antenna, the second antenna generating a time varying voltage in response to the signal; and
      ii) a second photomixer electrically coupled to the second antenna and optically coupled to the first and the second light source, the second photomixer generating a current signal in response to the time varying voltage generated by the second antenna.

2. The transceiver of claim 1 wherein a conductance of the first and second photomixer is modulated at the difference frequency in response to the first and the second light source.

3. The transceiver of claim 1 further comprising a voltage source coupled to the first photomixer, the voltage source biasing the first photomixer to generate a current having a frequency approximately equal to the difference frequency.

4. The transceiver of claim 1 further comprising a transimpedance amplifier electrically coupled to the second photomixer that generates a DC voltage in response to the current signal generated by the second photomixer.

5. The transceiver of claim 1 wherein at least one of the first or the second photomixers comprises a low-temperature-grown GaAs.

6. The transceiver of claim 1 wherein the first and the second photomixer are embedded into a transmission line.

7. The transceiver of claim 6 wherein the transmission line is a co-planar waveguide.

8. The transceiver of claim 1 wherein at least one of the first or the second light source comprises a distributed-Bragg-reflector diode laser or a distributed-feedback diode laser.

9. The transceiver of claim 1 wherein at least one of the first and second antenna comprises a spiral antenna.

10. The transceiver of claim 1 wherein at least one of the first and the second antenna comprises a planar antenna or a horn antenna.

11. The transceiver of claim 1 further comprising a lens coupled to at least one of the first and the second antenna, the lens directing the signal radiated by the first antenna.

12. The transceiver of claim 1 further comprising a processor in communications with the second photomixer, the processor processing the current signal generated by the second photomixer.

13. The transceiver of claim 1 further comprising an intermediate frequency amplifier electrically coupled to the second photomixer that amplifies intermediate frequencies generated by the second photomixer.

14. A method of transmitting and receiving radiation, the method comprising:
   a) providing a first light source that generates a first beam of light at a first frequency;
   b) providing a second light source that generates a second beam of light at a second frequency;
   c) modulating a conductance of a first photomixer at a difference frequency approximately equal to the difference between the first and the second frequencies in response to the first and the second light beam to generate a signal having the difference frequency;
   d) transmitting the signal;
   e) receiving the signal transmitted;
   f) generating a time varying voltage in response to the signal received;
   g) modulating a conductance of a second photomixer at the difference frequency in response to the first and the second light beam; and
   h) generating a current signal in response to the time varying signal received by the second antenna and the modulated conductance of the second photomixer.

15. The method of claim 14 wherein the current signal generated in step g) comprises a time-varying term having approximately twice the difference frequency and a DC term.

16. The method of claim 14 further comprising the step of detecting a DC voltage in response to the current signal generated in step g).

17. The method of claim 14 further comprising the step of changing at least one of the first or the second frequency and repeating steps c) through h).

18. The method of claim 17 wherein the step of changing at least one of the first or the second frequency comprises changing the operating temperature of at least one of the first or the second light source.

19. The method of claim 14 further comprising the step of measuring a Doppler shift in the time varying voltage generated in step e).

20. A method of performing real time spectroscopy comprising:
   a) providing a first light source that generates a first beam of light at a first frequency;
   b) providing a second light source that generates a second beam of light at a second frequency;
   c) modulating a conductance of a first photomixer at a difference frequency approximately equal to the difference between the first and the second frequencies in response to the first and the second light beam to generate a signal having the difference frequency;
   d) transmitting the signal through a medium to be analyzed;
   e) receiving the signal;
   f) generating a time varying voltage in response to the signal;
   g) modulating a conductance of a second photomixer at the difference frequency in response to the first and the second light beam;
   h) generating a current signal in response to the time varying signal received by the second antenna and the modulated conductance of the second photomixer;
   i) measuring at least one of amplitude or phase of the current signal; and
   j) determining at least one of absorption or dispersion characteristics of the medium from the amplitude or phase measurement.

21. The method of claim 20 wherein the medium is a gas.

22. The method of claim 20 further comprising the step of determining a presence of a particular medium from the absorption or dispersion characteristics.

23. The method of claim 20 further comprising the step of changing at least one of the first or the second frequency and repeating steps c) through j).

24. The method of claim 20 wherein the step of determining at least one of absorption or dispersion characteristics of the medium comprises measuring a frequency chirp in the current signal.

25. A method of imaging, an object, the method comprising:
   a) providing a first light source that generates a first beam of light at a first frequency;
   b) providing a second light source that generates a second beam of light at a second frequency;
   c) modulating a conductance of a first photomixer at a difference frequency approximately equal to the difference between the first and the second frequencies in response to the first and the second light beam to generate a signal having the difference frequency;
   d) transmitting the signal through an object to be imaged;
   e) receiving the signal transmitted;
   f) generating a time varying voltage in response to the signal;
   g) modulating a conductance of a second photomixer at the difference frequency in response to the first and the second light beam;
   h) generating a current signal in response to the time varying signal received by the second antenna and the modulated conductance of the second photomixer;
   i) measuring at least one of amplitude or phase of the current signal; and
   j) processing at least one of the amplitude or phase of the current signal to form an image of the object.

26. The method of claim 25 further comprising the step of converting the current signal into digital data.

27. The method of claim 25 further comprising the step of down converting the current signal.

28. The method of claim 25 wherein the step of transmitting the signal through the object comprises imaging the signal to a predetermined position on the object.

29. The method of claim 25 wherein the step of receiving the signal transmitted through the object comprises imaging the signal to a detector.

30. A method of network analysis comprising:
   a) providing a first light source that generates a first beam of light at a first frequency;
   b) providing a second light source that generates a second beam of light at a second frequency;
   c) modulating a conductance of a first photomixer at a difference frequency approximately equal to the difference between the first and the second frequencies in response to the first and the second light beam to generate a signal having the difference frequency;

d) transmitting the signal to a network to be analyzed;

e) receiving the signal;

f) generating a time varying voltage in response to the signal;

g) modulating a conductance of a second photomixer at the difference frequency in response to the first and the second light beam;

h) generating a current signal in response to the modulated conductance of the second photomixer;

i) measuring at least one of amplitude or phase of the current signal; and j) processing at least one of the amplitude or phase of the current signal to determine at least one of a transmission or a reflection parameter of the network.

31. The method of claim 30 wherein the step of receiving the signal transmitted from the network comprises receiving the signal reflected from the network.

32. The method of claim 30 wherein the step of receiving the signal transmitted from the network comprises receiving the signal transmitted through the network.

33. The method of claim 30 wherein the at least one of a transmission or a reflection parameter comprises a scattering parameter.

* * * * *